(12) United States Patent
Mahtani

(10) Patent No.: US 6,221,603 B1
(45) Date of Patent: Apr. 24, 2001

(54) ROLLING CIRCLE AMPLIFICATION ASSAY FOR NUCLEIC ACID ANALYSIS

(75) Inventor: Melanie M. Mahtani, Palo Alto, CA (US)

(73) Assignee: Molecular Dynamics, Inc., Sunnyvale, CA (US)

( * ) Notice: Subject to any disclaimer, the term of this patent is extended or adjusted under 35 U.S.C. 154(b) by 0 days.

(21) Appl. No.: 09/498,585

(22) Filed: Feb. 4, 2000

(51) Int. Cl.$^7$ .............................. C12Q 1/68; C07H 21/04; C07H 21/02; C12N 15/00
(52) U.S. Cl. ..................... 435/6; 536/23.1; 536/24.3; 935/76; 935/77; 935/78
(58) Field of Search ................. 435/6; 536/23.1, 536/24.3; 935/76, 77, 78

(56) References Cited

U.S. PATENT DOCUMENTS

| | | | |
|---|---|---|---|
| 5,648,245 | 7/1997 | Fire et al. | 435/91.1 |
| 5,714,320 | 2/1998 | Kool | 435/6 |
| 5,846,726 | 12/1998 | Nadeau et al. | 435/6 |
| 5,854,033 | 12/1998 | Lizardi | 435/91.2 |
| 5,866,337 | 2/1999 | Schon | 435/6 |
| 5,871,921 | 2/1999 | Landegren et al. | 435/6 |

FOREIGN PATENT DOCUMENTS

WO92/01813 * 2/1992 (WO) .
WO99/09216    2/1999 (WO) .

OTHER PUBLICATIONS

Nilsson et al., Padlock Probes: Circularizing Oligonucleotides for Localized DNA Detection. Science 265: 2085–2088 (1994).*

* cited by examiner

*Primary Examiner*—Ethan Whisenant
(74) *Attorney, Agent, or Firm*—Thomas Schneck; David M. Schneck

(57) ABSTRACT

Method and reagents for analysis of nucleic acid sequences is disclosed. In this method a plurality of padlock probes is provided. Each padlock probe may hybridize to a locus on a target nucleic acid under hybridization conditions. If a targeted variant is present at the locus, the padlock probe may be ligated to form an amplification target circle. The amplification target circle acts as a template for production of tandem-sequence DNA. The tandem-sequence DNA may then be digested into non-tandem detection fragments which are subsequently separated and detected. The plurality of padlock probes are designed such that ligation of the probes, amplification of the target circle, and digestion of the tandem-sequence DNA subsequently produced, and detection may all be effected with the same set of reagents. Each probe targets a unique locus variant on the target nucleic acid sequence and produces a detection fragment that may be distinguished from detection fragments produced from other padlock probe in the plurality of padlock probes by using a fragment analysis detector.

28 Claims, 3 Drawing Sheets

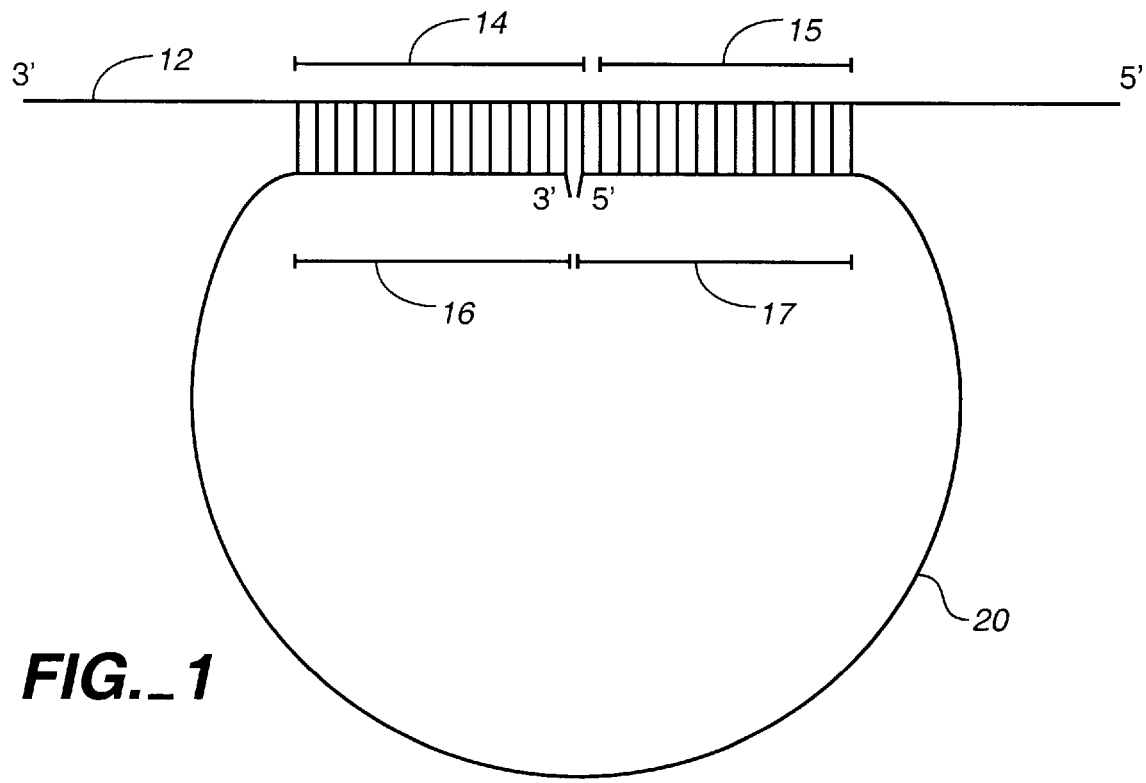
FIG._1
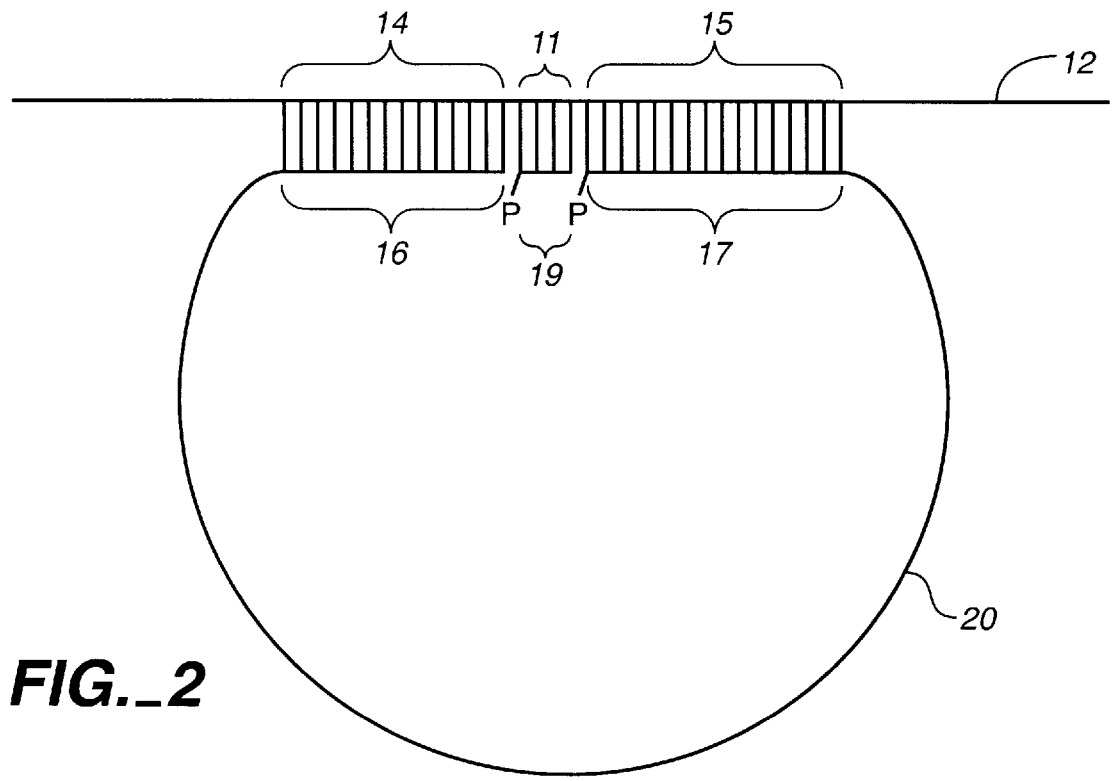
FIG._2

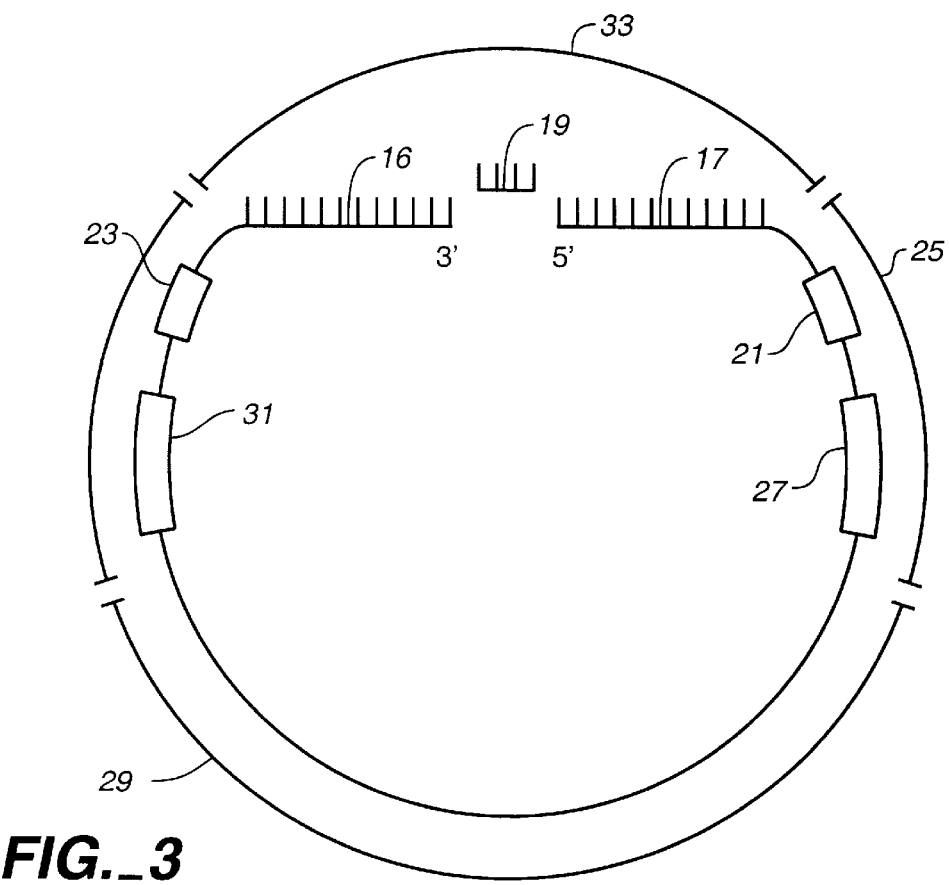
FIG._3
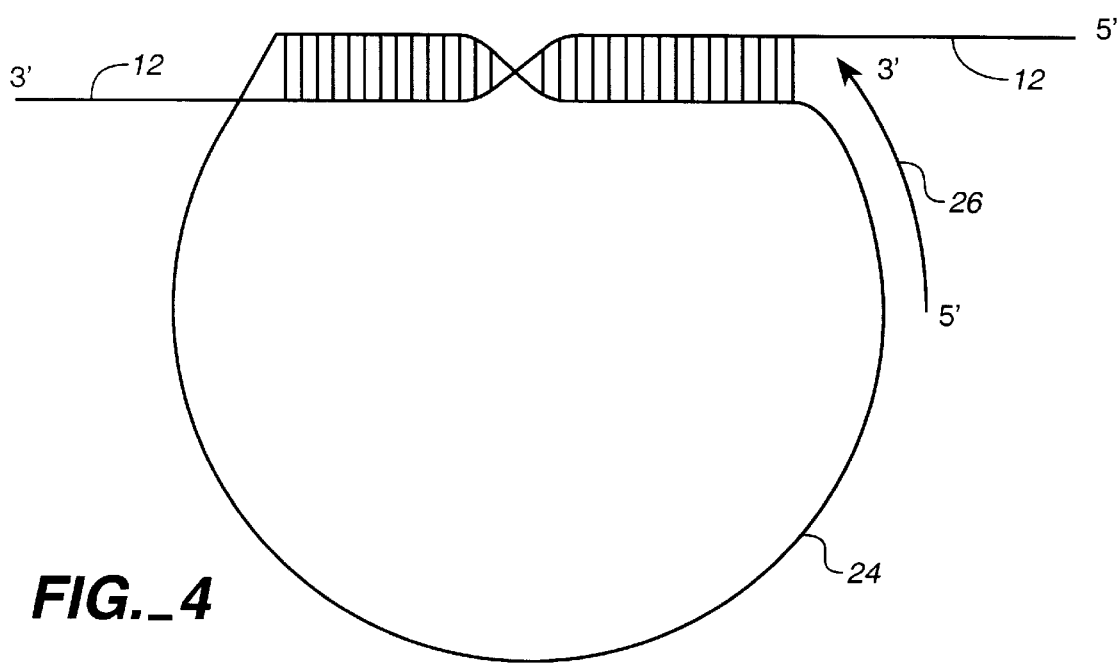
FIG._4

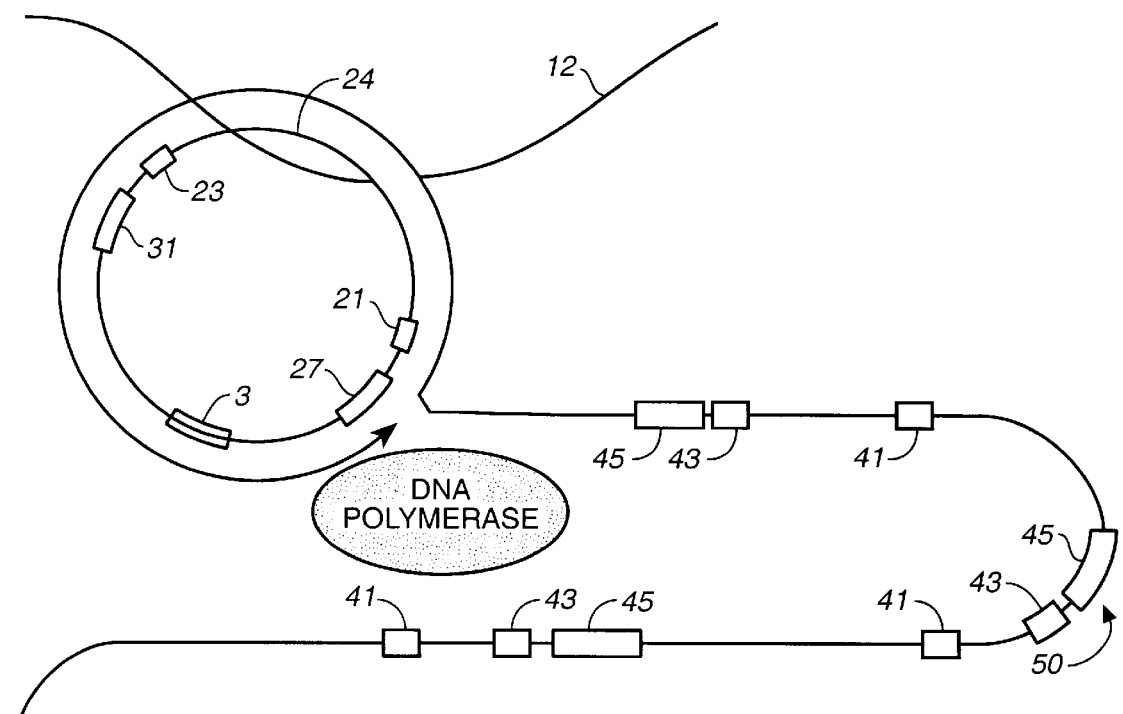
FIG._5
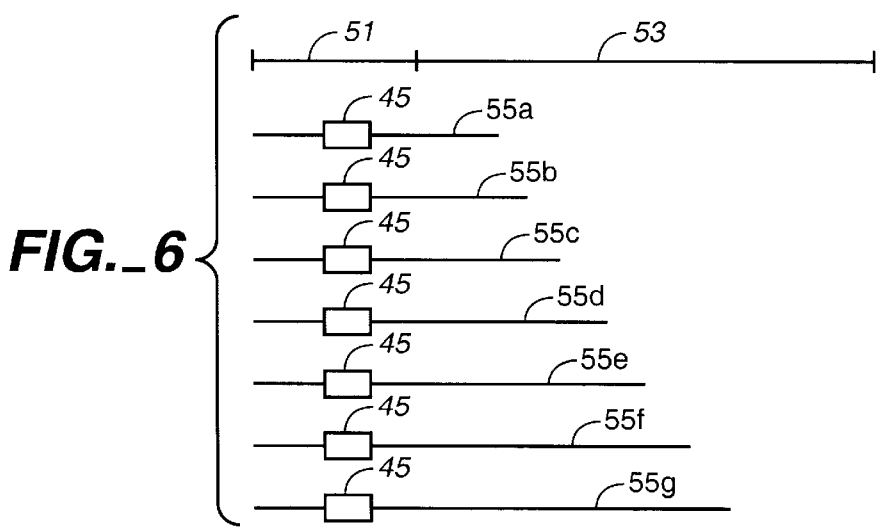
FIG._6

ROLLING CIRCLE AMPLIFICATION ASSAY FOR NUCLEIC ACID ANALYSIS

FIELD OF INVENTION

The present invention relates to analysis of nucleic acids and specifically to the detection of nucleic acid variants.

BACKGROUND OF INVENTION

There is a significant need for the rapid, low-cost analysis of nucleic acid sequences. The extensive size and variability of nucleic acid samples have presented challenges for the analysis of genetic variation. The human genome contains over three billion base pairs, which contain the sequences for tens of thousands of genes. Variation at individual nucleotides is common. Single nucleotide polymorphisms, a set of single nucleotide variants at a genomic loci, are distributed throughout a genome. In the human genome, such single nucleotide variation occurs relatively frequently, about once in every 200–1000 bases, resulting in millions of single nucleotide polymorphisms in the human genome. To determine the identity of all single nucleotide polymorphism variants within a population would require a very large number of reactions for a very large number of individuals. If a single nucleotide polymorphism exists at a locus with a gene, the variant may result in a phenotypic difference. In addition to the analysis of genomic DNA, information on gene expression or alternate splice forms of mRNA may be gathered from the analysis of mRNA or cDNA. Analysis of DNA often requires screening DNA libraries, the analysis of genomic segments stored in an array of plasmid, cosmid or viral vectors. Bacterial plasmids and viral genomes are also sources of nucleic acid sequences that often require analysis.

The rapid advances in sequencing have produced a flood of known sequences and known polymorphisms. These advances potentially have diagnostic, therapeutic and research applications. However, such applications require the ability to rapidly analyze the genotype of a large number of samples. With this new sequence information has come a greater need for the ability to rapidly and accurately assay genetic variation in nucleic acid sequences.

Presently there are a number of assays for detection of nucleic acid sequences. These assays are sensitive and can produce detectable results with 100 target molecules or fewer. These assays are also specific, allowing accurate detection of specific sequences. The polymerase chain reaction (PCR) is one such method for amplification and detection of a specific sequence. This method consists of repeated cycles of denaturing a template strand of DNA, annealing matched primer pairs to the DNA, and extending the DNA from the primer using a DNA polymerase. A matched set of primers is used to amplify the sequence between the locations where the primers anneal. After each cycle, the resulting copy may act as a template for additional copying, allowing exponential amplification. Following the amplification of a DNA sequence, the sequence can be analyzed by sequencing or by restriction fragment analysis.

Ligase chain reaction (LCR) is another genetic analysis procedure. In this method, sequence-specific ligation is effected to determine the presence of a genetic variant. The sequence-specific ligation is preformed in cycles. In each cycle following hybridization and ligation, the joined fragments are subjected to a heat cycle to separate the ligated fragments from the parent strand. The fragments can serve as a template for further sequence specific ligation. Like PCR, LCR provides the exponential amplification of a target sequence.

Both PCR and LCR require temperature cycling to effect the reaction. Thermal cycling requires time for each cycle and requires dedicated instruments to generate the thermal cycles.

To generate the probes and primers for PCR and LCR, circularized DNA amplification has been used. In PCT filing WO 99/09216, Kool discloses a method of using rolling circle amplification to generate concatameric DNA. A single stranded, circularized template is combined with a polymerase and nucleotide triphosphates to yield a concatamer comprised of repeating oligonucleotide sequences. If the template has a site complementary to a restriction enzyme site, the concatamer may be digested into oligonucleotides of a single length. Either the concatamer or the digested oligonucleotides may be subsequently used, for example as probes.

One alternative for the detection of nucleic acid polymorphisms is the use of rolling circle amplification systems. In such a system, a probe is hybridized to a target nucleic acid sequence at a specific genomic locus. If the nucleic acid sequence targeted is present, the ends of the probe will hybridize with the target nucleic acid in such a way that the ends may be ligated together. This probe would then become an amplification target circle which could serve as the template for the generation of tandem-sequence DNA. Included as part of the probe is a primer complementary region. A primer added to the reaction mixture would hybridize onto the probe. If the amplification target circle is formed, a DNA polymerase which begins to produce a DNA transcript of the circle would then produce repeated copies of the amplification target circle.

In U.S. Pat. No. 5,871,921, Landegren et al. describes one method in which rolling circle amplification may be used for detection of genomic variants. In the assay, a detectable nucleic acid probe is hybridized to a single stranded nucleic acid target. The probe will hybridize with the target nucleic acid only if the targeted sequence is present. The hybridized probe ends are then covalently connected to form a continuous loop of probe nucleic acid. Following the formation of the continuous loop, the probe/target is subjected to conditions that would remove probes that did not form a continuous circuit, such as denaturing the probe/target hybrid or subjecting the probe to exonuclease activity to remove the non-cyclized probes. The target molecule may then be detected by determination of the presence of the interlocking catenated probe. Analysis of the reaction product requires separation of target DNA that does not have a tethered ligated probe from target DNA that does have the tethered ligated probe.

An alternative method of using the rolling circle amplification process is disclosed in U.S. Pat. No. 5,648,245 to Fire et al. The reference describes a four-step process for generating a concatamer library. In the procedure, the first step is to generate an amplification target circle by annealing ends of a padlock probe to a target nucleic acid sequence followed by ligation of the ends of the padlock probe to form a continuous loop. Once the amplification target circle is formed, the second step is to create a single stranded tandem-sequence DNA by rolling circle amplification of the amplification target circle. The third step requires converting the single stranded tandem-sequence DNA to double stranded tandem-sequence DNA. Finally, the double stranded tandem-sequence DNA is cloned or used for in vitro selection.

U.S. Pat. No. 5,866,377 to Schon uses rolling circle amplification as a method to detect variants in a nucleic acid sequence. In this method, a padlock probe hybridizes to a single stranded nucleic acid such that the ends are adjacent to each other. A ligase then joins the ends of the probe. The ligation reaction will be carried out only if the target nucleic acid contains a specific variant base at the locus near the end base of one of the probe ends. Detection of the presence of the catenated probe on the target nucleic acid indicates the presence of the specific variant. U.S. Pat. No. 5,854,033 to Lizardi describes a similar assay where the catenated probe is used to produce tandem-sequence DNA by rolling circle amplification. The tandem sequence is detected to determine the amount of target sequence present.

The use of rolling circle amplification presents certain advantages. The ligation creates a unique circularized template. The nature of the reaction is highly specific to the target nucleic acid of interest. The two probe hybridization regions assure that the hybridization to the target will be highly specific. In addition, rolling circle amplification may be used to detect genomic variants or to identify sequences present in a nucleic acid sample, such as in gene expression assays. Furthermore, the reaction is isothermal, eliminating the need to use a thermal stable polymerase or a temperature cycling apparatus. The thermal cycling process takes time with each cycle requiring heating blocks to change and transmit a temperature change.

It would be beneficial if a rolling circle assay could be used in a multiplex format where a number of reactions could be run in a single assay container. This reaction would produce a pool of DNA fragments with size and/or label differences which could be analyzed on currently used DNA analytical instruments.

An object of the invention is to adapt the rolling circle amplification into a multiplex format to greatly increase the assay throughput.

A further object of this invention is to provide methods and reagents for adapting the rolling circle amplification for detection of genomic variation at specific loci as well as useful in expression assays.

It is a further object for the invention to provide these features in a high throughput assay that is both rapid and accurate.

It is an object that the assay should use conventionally available reagents and may yield results by analysis using conventionally available analytical systems.

It is an object to reduce the cost and reagent requirements of processing each reaction by allowing analysis of a number of genetic variants in a single assay mixture using a single set of reagents to process numerous samples.

A further object of the invention is to provide an assay in which many loci can be simultaneously assayed on a single target nucleic acid or set of nucleic acids, greatly reducing the amount of target nucleic acid required for analysis of numerous loci.

It is also an object of the invention to provide the amplification reaction which is isothermal.

SUMMARY OF THE INVENTION

The above objects are achieved through methods and reagents for the high throughput analysis of genetic loci using padlock probes. In this assay, sets containing a plurality of probes are used to assay target nucleic acid sequences, such as genomic DNA, plasmids, viral genomic DNA, viral genomic RNA, cDNA or mRNA. Through the use of these sets of probes, a set of detection fragments are produced. The detection fragments are distinguishable by size and/or detectable label. Each detection fragment is produced if a target nucleic acid targeted by a corresponding probe is present. Multiplex assay by detection of size and detectable label allows detection of numerous fragments in a single reaction and analytical separation.

Each probe in the set of probes is comprised of two hybridization end regions and a stuffer region between the end regions. These hybridization end regions are complementary to a specific locus on a target nucleic acid sequence. Part of this stuffer region is a sequence complementary to a primer. The primer complementary sequence is the same for each padlock probe of the plurality of padlock probes.

Each probe of the plurality of probes is designed to hybridize to the target nucleic acid strand at a locus. When the probes hybridize to the target nucleic acid to form a probe/target duplex, the ends of each probe or the bases between the ends of the probe will be at the site of the locus of interest.

The probe/target duplex is next incubated with a ligase under ligation conditions. The ligation conditions generally involve adding a ligase to the reaction mixture to ligate the padlock probes into circular strands to form amplification target circles. However, ligation will occur only if the target nucleic acid sequence has a specific composition at the location where the padlock probe hybridizes onto the target nucleic acid. The padlock probe may be designed so that the ends of the padlock probe are separated by a gap. The gap must be filled for the ligation to occur. Included in the ligation mixture with the padlock probe would be a potential gap filler, such as a nucleotide base or a small oligonucleotide. If the target nucleic acid sequence has the allele of interest, the gap filler will hybridize onto the target to fill the gap. The ligase will then ligate together the adjoining ends of the gap filler and the ends of the probe to form a continuous amplification target circle. In an alternative embodiment, the gap is filled using a polymerase and nucleotide triphosphates before the probe ends are ligated together. The padlock probes could also be designed to anneal to the target strand without a gap. The probe would hybridize to the target strand if the targeted hybridization sequence was present on the target nucleic acid or if the ends of the probe were complementary to the target nucleic acid sequence.

The plurality of padlock probes would hybridize to a plurality of loci on the target nucleic acid sequence. Under the ligation conditions, if the target nucleic acid sequence has the genotypic variant of interest, the probe will be ligated into an amplification target circle. The amplification target circles that are generated act as templates for the generation of tandem-sequence DNA. All of the probes that have been ligated to form amplification target circles may then be amplified in a single reaction by adding a primer and a DNA polymerase to the mixture. The DNA polymerase will attach at the primer sequence and will produce a strand of tandem-sequence DNA from the amplification target circle template. Each padlock probe that was ligated to form an amplification target circle will produce a unique tandem-sequence DNA strand. The tandem-sequence DNA is then digested to form non-tandem fragments. The plurality of padlock probes may be designed such that one enzyme, such as a restriction enzyme, may be used to digest all of the tandem-sequence DNA. Each padlock probe generates unique non-tandem fragments and each probe is designed such that the non-tandem fragments produced differ in length from the non-tandem fragments produced by any other padlock probe. In one embodiment, the padlock probes are designed to produce non-tandem fragments of 30–100 bp in length with each fragment differing in length from any other fragment by two base pairs.

The fragments are labeled with a detectable label and detected by separation by size. In one embodiment, the fragments are labeled with a direct DNA stain and are analyzed using a capillary array electrophoresis system. An alternative to using a direct DNA stain is to design the probes such that the resulting non-tandem detection fragments contain a sequence which is complementary to a secondary probe. After generating non-tandem fragments, the fragments would be incubated with the secondary labeled probe which would anneal to the fragments and allow detection. In one embodiment, a polymerase and nucleotide triphosphates are added to extend the secondary probe to form a double stranded detection fragment. In another embodiment, the use of probes with two or more different optical labels allows greater detection throughput by providing a method in which two fragments of the same size may be distinguished by the detectable label.

BRIEF DESCRIPTION OF THE DRAWINGS

FIG. 1 is a diagram of a padlock probe hybridized to a target nucleic acid sequence.

FIG. 2 is a diagram of a padlock probe with a gap oligonucleotide hybridized to a target nucleic acid sequence.

FIG. 3 is a diagram of a padlock probe with specific sections of the probe indicated.

FIG. 4 is a diagram of a padlock probe ligated to a target nucleic acid sequence after hybridization to the target nucleic acid.

FIG. 5 is a diagram of rolling circle amplification of an open circle probe by a strand displacement DNA polymerase.

FIG. 6 is a diagram of a set of non-tandem fragments generated by a plurality of padlock probes.

DETAILED DESCRIPTION OF THE INVENTION

The present invention enables the rolling circle amplification reaction to be used for the high throughput analysis of nucleic acid sequences. In this method a number of genetic variants or expressed genes may be assayed in a single reaction. The assay should prove especially valuable in assay of single nucleotide polymorphism alleles.

In the present invention, a multiplex reaction using rolling circle amplification increases the through-put analysis of target nucleic acid sequences. The assay of the present invention would require:

1. Providing at least one set of padlock probes in each assay container. Padlock probes would be designed so that each padlock probe would have target hybridization end regions designed for the detection of one variant, at one locus. Between the end regions of each probe is a stuffer region which has a constant region and a variable region. The constant region would be the same for all of the probes in a set, and would contain the sequence complementary to an amplification primer. The variable region would vary in length for each probe and would have a sequence which is target specific on each probe. In one embodiment, the stuffer region also has a sequence complementary to a detection probe.

2. Hybridizing the padlock probe onto the target nucleic acid.

3. Adding ligase to the padlock probe/target nucleic acid mixture and incubating the mixture under ligation conditions to promote ligation of the ends of the probe to form an amplification target circle. If the sequence of interest is present, the ligase will convert the probe to a closed loop to form an amplification target circle.

4. Adding a replication primer and DNA polymerase to the assay mixture. If the amplification target circle was formed, the circle will serve as a template for the production of tandem-sequence DNA consisting of repeated copies of the amplification target circles. Only the probes present at the variant of interest will be ligated into amplification target circles and be available as a template for the formation of tandem-sequence DNA. Because each probe had an identical primer complementary sequence, only a single primer needs to be added to amplify all of the amplification target circles present.

5. Cutting each tandem-sequence DNA into non-tandem fragments. The set of padlock probes is designed such that the tandem-sequence DNA, when cut into non-tandem fragments, will have a different length for each padlock probe in the set. The padlock probes have stuffer regions of varying lengths. Preferably the stuffer regions are all derived from the same sequence and the stuffer regions of varying lengths have the same ratio of nucleotide components. Following the ligation procedure, the amplification target circles will also have different lengths. When the tandem-sequence DNA is cut into non-tandem fragments, the lengths of the fragments generated by each probe in a set will be different. Fragment size may range from 20–150 bases, allowing rapid detection in a preferred separation range.

6. Separating and detecting the non-tandem DNA fragments. The fragments are each of different length, allowing separation by size on a number of known analytical systems. Detection of the fragment indicates the presence in the target nucleic acid of the variant of interest. Preferably a fragment size ladder is included with the separation and detection of non-tandem fragments to help identify the presence or absence of generated fragments. The fragment may be detected by direct stain or indirect label. If an indirect label is used, a detection probe complement present in the constant region of the stuffer section of each probe would allow a single labeled detection oligonucleotide to be used to detect the target sequence in the fragments produced by a set of padlock probes.

Several levels of multiplexing are possible using this system. First, each set of probes produces corresponding detection fragments which vary by size. Second, additional sets of probes may be used in a single reaction container if each set of probes produces detection fragments which use a different detectable label. For example, two fragments of the same length may be distinguished by an optical detector if each fragment is associated with a separate optical label. Multiple sets of probes may be used simultaneously in a single reaction container. The reagents used with each probe could be the same except for the labeling reagent. Third, further multiplexing could be achieved by pooling target nucleic acid. Fourth, the detection fragments are sufficiently small to allow for multiple groups of fragments to be loaded onto a separation system such as a capillary in an electrophoresis system and continuously separated and detected. These four levels of multiplexing, alone or in combination, greatly increase throughput in analyzing target nucleic acid fragments.

Using this method of detection, a large number of loci or variants may be assayed at one time. For example, a set of probes may be designed to assay for 30 separate loci. This assay may be effected in a single reaction container and analyzed on a single system. These 30 loci could be generated in a small reaction container such as a microplate well, and would use the same reagents for ligation, amplification and restriction into non-tandem fragments. In addition, the amount of target nucleic acid in each reaction container is used to simultaneously assay numerous loci. Each reaction requires about 50 ng of target nucleic acid. The ability to simultaneously assay multiple loci in a single reaction container greatly reduces the cost of each locus assay. The resulting fragments may be analyzed in a single separation length (e.g. single capillary in a capillary electrophoresis array) in which the fragments are separated by length.

A number of references contain instruction on probe components, ligation, and ligation specificity, and amplification. These references include U.S. Pat. Nos. 5,871,921; 5,648,245; 5,866,377; and 5,854,033 all hereby expressly incorporated by reference herein.

The reagents and methods of the invention allow for the high throughput analysis of a number of different genetic loci at the same time. The analysis can determine the presence or expression of a gene of interest. Alternatively, the analysis can detect a polymorphic variation at a specific site of interest.

I. The Padlock Probes

The padlock probes are designed to allow for the assay of a single variant each. Each padlock probe is a linear, single-stranded DNA molecule which generally will range between 50 and 250 bases long. Each padlock probe has a 5' phosphate terminal end and a 3' hydroxyl terminal end. This enables the ends to be ligated if brought into alignment. In addition, the ends could be extended with a polymerase.

In the present invention, the padlock probes are designed and used as sets of probes. Each probe in a set of padlock probes will have regions specific to that probe as well as regions common to every padlock probe in a set.

The padlock probe is comprised of two sections, the target hybridization end regions, and the stuffer region. One target hybridization end region is located at each end of the padlock probe, with the stuffer section located between these two end regions. The stuffer section has a constant region and a variable region. The constant region is same for each probe in the set of padlock probes. The constant region includes the primer complementary sequence, the restriction enzyme complementary region, and the detection probe complementary region. This allows subsequent amplification, restriction and detection using a single set of reagents. The variable stuffer region varies in size from each probe in a set of probes.

A. Target Hybridization End Regions

The target hybridization end regions are the two ends of the padlock probe. These regions are designed to form a specific and stable hybrid with a specific sequence of a target nucleic acid. Each target hybridization end region preferably is between 10 and 35 nucleotides in length. The target hybridization end regions are complementary to a specific target nucleic acid sequence. Target hybridization end regions are specific to a gene locus and may be designed to be specific to a particular variant at the locus.

As shown in FIG. 1, the target hybridization end regions 16, 17 of padlock probe 20 are complementary to a sequence of the target nucleic acid 14, 15 such that when the ends of the probe anneal to the target nucleic acid, the 3' end of the padlock probe and the 5' end of the padlock probe are proximate to each other. Proximate is defined to mean within 10 nucleotides.

The end regions of a padlock probe are designed to have one of two orientations on the target nucleic acid. The first orientation, shown in FIG. 1, is where the probe ends are in adjacent configuration. Probes of this design could detect a polymorphism if the polymorphism occurs at the last two bases in the end regions. In such assays, the probe ends would hybridize to the target nucleic acid sequence and the ends would be in alignment if the variant of interest is present. However, if the variant of interest is not present the target hybridization end region will not be wholly complementary to the target nucleic acid strand and at least one base pair is a mismatch. The ends will not be brought into alignment to allow for ligation. By designing the padlock probe so that the mismatch would occur at the last base at the 3' end of the probe, detection of single nucleotide variants is possible.

It is also possible to use a probe whose ends come into adjacent alignment simply to detect the presence of a sequence of interest, for example in screening a DNA library or in an assay of expression. In such assays, the ends of the probe will only hybridize to the target nucleic acid if the sequence of interest is present. If the sequence of interest is not present, the probe would not bind to the target nucleic acid at all.

In the second orientation, shown in FIG. 2, the padlock probes in a set 20 are designed such that the ends of the probe 16, 17 are separated by a gap. This is a second method to discriminate between variants at a polymorphic locus. The gap preferably is 10 bases long or shorter. If a gap is used, a gap-filling nucleotide or oligonucleotide 19 will anneal to the target nucleic acid 12 between probe ends 16, 17. If a single nucleotide variant is to be detected, the probe should be designed such that the variant base is located opposite the terminal base of the gap oligonucleotide 3' end or the terminal base of the probe hybridization end 3' terminus.

Alternatively, it is possible to eliminate the gap filling oligonucleotide. Instead a DNA polymerase and nucleotide triphosphates (dNTP) are combined with the probe target duplex. The DNA polymerase will attack at the 5' end of the target hybridization region and covalently join bases filling in the gap to the 3' end of the probe.

B. Stuffer Regions

The stuffer regions are located on the probe between the target hybridization end regions. The stuffer regions have a constant and a variable region. The constant region is identical for all of the probes in a set. In contrast, the variable region varies in length for each padlock probe in the set, although the variable region for each probe in a set may be generated from varying length of the same source DNA. The variable region is preferred to have essentially the same ratio of base composition (e.g. C/G ratio) for each of the varying lengths in a set of probes.

In the constant region, each padlock probe in a set of probes will have a replication primer complementary region, a restriction site complementary region, and, optionally, a detection probe complementary region.

1) The Replication Primer Complementary Region

The replication primer complementary region is a sequence of the padlock probe which complements a replication primer. The replication primer is an oligonucleotide which anneals to the amplification target circle allowing a DNA polymerase to attach to the target circle. In a set of padlock probes, the replication primer complementary region is the same sequence for all of the padlock probes in the set. In addition, the primer complementary region is in the same location relative to the padlock probe ends for all of the probes in the set. The replication primer complementary sequence and its cognate primer may have any designed sequence as long as they are complementary to each other but not complementary to other sequences of the padlock probe. Having a primer complementary sequence which is between 15–20 bases long helps ensure that the primer will be sufficiently long to have a unique sequence and hybridize selectively to the padlock probe. Although the replication primer complementary region may be present at any location on the stuffer sequence of the padlock probe, it is preferred to have this primer location proximate to the 3' target hybridization end region. This position of the primer ensures that the DNA polymerase will begin transcription moving toward the probe target hybridization end regions.

2. Restriction Site Complementary Region

The constant region also has a region complementary to a restriction enzyme. This region produces on the subsequently generated tandem-sequence DNA a restriction enzyme site. The subsequently generated tandem-sequence DNA with this restriction site may be digested with a restriction enzyme into non-tandem fragments of equal length. Each set of padlock probes would have the same restriction enzyme site complementary region. This region is proximate to the target hybridization end regions.

In one embodiment, each probe would have two restriction enzyme site complementary regions. Each complement to the restriction site would be located in the stuffer region and proximate to one of the target hybridization end regions. In this embodiment, the resulting padlock probes would, when ligated, act as a template for production of tandem-sequence DNA. The tandem-sequence DNA would then be cut, using two restriction enzymes, into two fragments: a detection fragment and a fragment complementary to the target hybridization end regions. This allows for greater uniformity in the detection fragments. One advantage of this embodiment is the guanine/cytosine (g/c) ratio in the detection fragment may be kept uniform for each probe in a set of probes. In the target hybridization end regions, the g/c ratio may be different for each probe. By excluding the target hybridization end regions from the detection fragment, the base composition of the fragments produced by a set of padlock probes can be made uniform.

The restriction site may be the site at which a site-specific nuclease cleaves a polynucleotide chain. The restriction enzyme may cut double- or single-strand DNA. If a double-strand cutting enzyme is used, an oligonucleotide must be included with this reaction to create double-stranded regions on the tandem-sequence DNA at the restriction site. The detection probe may be designed to form double-stranded DNA at the restriction site. The detection probe, after annealing, would be cut by the restriction enzyme such that the detectable label on the probe remained on the fragment.

3. Detection Probe Complementary Region

The detection probe complementary region may optionally be included in the constant stuffer region of each padlock probe in a set. This region has a sequence which is the same as that of an oligonucleotide probe. The oligonucleotide probe may be used to detect subsequently generated detection fragments. The detection probe should be sufficiently long to promote specific hybridization with the detection fragments.

4. Variable Stuffer Region

The variable stuffer region is a sequence on each probe which varies in size between each probe. Preferably, the probes have uniform, incremental variations. A size difference of two bases is preferred.

FIG. 3 shows a representation of the features of a padlock probe. The target hybridization end regions 16, 17 and gap-filling oligonucleotide 19 comprise a region 33 unique to each padlock probe. This sequence is designed to hybridize with a complementary region on the target nucleic acid. The sequence of the probe outside region 33 comprises the stuffer section of the probe. The stuffer segment is divided into a constant region 25 which is identical for every probe in a set of padlock probes and a variable region 29 which is of a unique size for each padlock probe in a set.

Within the constant region 25 of every stuffer section are sequences which are common to every padlock probe in a set of padlock probes. These include restriction enzyme site complementary regions 21, 23, a primer complementary region 27 and a detection probe complementary region 31. These identical elements allow the steps of amplification, restriction and labeling to occur under isothermal conditions using a single set of reagents with all steps occurring in a single reaction container. The variable region 29 has a length which is unique for each padlock probe in a set of padlock probes.

In designing padlock probes in accordance with the present invention, several factors must be considered:

1. Probe length. The total length of the probe (or the detection fragment within the probe) preferably should range from 30–100 bases. This allows production of non-tandem fragments in the optimal detection range for a number of different detection systems.

2. The probes should not have regions which are self complementary. Self-complementary regions would result in parts of the probe being unable to hybridize onto other sequences. This criteria is satisfied if the designed probe has no sequence that is complementary to any other probe continuous sequence six nucleotides long or longer.

3. The g/c ratio should be the same for each probe in a set. An unequal g/c ratio could result in different migration rates in some analytical systems. This can be avoided by using two restriction enzyme site complementary regions to produce a detection fragment as described above. In this manner, only the stuffer region is analyzed for length variation, while the target hybridization end regions are not. This allows control of the g/c ratio in the detection fragment.

4. It is preferred that the variable stuffer sequences be generated from the same source DNA. For example, plasmid may provide the DNA source with each probe in a set of probes designed to have a variable amount of the plasmid.

II. Method

The method of the present invention allows the high throughput analysis of a large number of nucleic acid variants in a single reaction. Method can be automated to produce even higher throughput. The detailed steps of the method are as follows.

1. Provide a padlock probe

A set of padlock probes is provided, where each padlock probe detects a genomic locus or one variant at a locus. Sets of probes may be used alone or in combination. If sets of padlock probes are used in combination, it is preferred that the padlock probes in all the sets have the same primer complementary regions, the same restriction site complementary regions, and different detection probe regions for each set. Each different probe region is associated with a unique detectable label. In this manner, different sets of padlock probes may generate detection fragments which are the same size. Each set of padlock probes may be designed to incorporate a unique detection signal, such as different fluorescent dyes, into the resulting detection fragment. Two sets of probes producing fragments of the same size may be used together and distinguished by the unique detection signal associated with each different set of probes.

The probe, as well as other oligonucleotide sequences used in the assay, are generated by conventional means. These methods include the digestion, isolation, and ligation of oligonucleotide fragments, or synthetic generation using a DNA synthesizer.

2. Hybridize onto target nucleic acid

The hybridization of the probe to the target nucleic acid strand initially requires ensuring that the target nucleic acid strand is in single stranded form. Double-stranded DNA can be heated to denature the DNA into single-stranded form. The temperature is then lowered to allow the probe ends to anneal to their designated target sequence. For example, heating to 94° will denature double-stranded genomic DNA, and cooling to 55° will allow the padlock probe ends to anneal onto the target nucleic acid.

As already noted, the target nucleic acids may come from any of a number of sources. The target nucleic acid sequence may be a DNA sample, an RNA sample, a mitochondrial DNA sample, a circular DNA sample such as a plasmid or cosmid, a chromosomal DNA sample, a viral DNA sample, or a cDNA sample. For analysis of gene expression, the sample could include a mRNA sample or a cDNA transcript. Different samples may be pooled and used as target DNA for the present multiplex analysis of nucleic acid sequences. For example, both genomic and plasmid bacterial DNA may be assayed together in a single procedure.

3. Ligation of probes and Formation of Amplification Target Circles

If the targeted variant of interest is present, the ends of the padlock probe will be aligned with each other or with the gap oligonucleotides ends, and may be joined by a ligase which has been selected to join the ends of the padlock probe. The ligase, if thermostable, may be included in the initial reaction mixture. The ligation reaction then produces an amplification target circle.

If the target nucleic acid is DNA, the ligase should be chosen to preferentially form phosphodiester bonds at nicks in double stranded DNA. Suitable ligases would include *E. coli* DNA ligase, T4 DNA ligase, Taq DNA ligase, and AMPLIGASE®. If the target nucleic acid is RNA, T4 DNA ligase is a preferred ligase since it is known to seal gaps in the DNA component of a DNA:RNA hybrid. Alternatively, it may be desired to use reverse transcriptase to transcribe the RNA into a DNA sequence. The ligase selected will determine the reagents needed to effect the ligation reaction. Most ligases require the presence of either ATP or NAD as an energy source. In addition, many ligases require a concentration of $Mg^{++}$.

The ligation forms a covalently closed circle of padlock probes which have ends oriented, which form amplification target circles. The relatively short length of the padlock probes helps reduce the risk of end-to-end ligation of probes that have not annealed to a target nucleic acid but are free in solution. In addition, selection of the ligase and reaction conditions may reduce end-to-end probe ligation. If AMPLIGASE® is used, ligation takes place at 60°. Under these conditions, a maximum of 1 in 1,000,000 probe terminal ends that are not bound to the targeted sequence will be ligated together. By using a gap oligonucleotide, two ligation reactions are required to seal the nicks and form a contiruious strand that could act as an amplification target circle. For a probe which has not annealed to the target nucleic acid, if one probe ligated with a gap oligonucleotide, the other end must also be ligated to form an amplification target circle. If the frequency of each end to end ligation is 1 in 1,000,000 the frequency of both ligations occurring is the square of this frequency: a rate of $1 \times 10^{12}$. By including an excess of gap oligonucleotides, the padlock probe self-ligation rate is reduced. This would result in very few amplification target circles being generated which are not a result of the padlock probe hybridizing to the target nucleic acid sequence.

FIG. 4 shows a padlock probe following ligation. The padlock probe has been sealed to form amplification target circle 24. Because the padlock probe forms a double helix with the target DNA, the padlock probe interlocks with the target nucleic acid 12. Following ligation, the interlocked padlock probe is sealed to a tethered amplification target circle 24. The amplification target circle 24 is tethered to the target nucleic acid at the location where the padlock probe hybridized to the target nucleic acid. If desired it is possible that, following ligation, the amplification target circles are denatured from the target DNA by heating or subjection to other denaturing conditions. Following denaturation, a second cycle of ligation of probes to target nucleic acid may occur at the targeted loci.

4. Rolling circle replication of amplification target circles

Once the padlock probes have been ligated to form amplification target circles, the circles may be continuously transcribed to form tandem-sequence DNA. This is done by adding a replication primer, and extending from the primer using a DNA polymerase.

As noted, the replication primer is an oligonucleotide, 15–30 bases long, which will anneal to a complementary region on the amplification target circle. The primer is not complementary to any other sequence of the amplification target circle and will form a specific and stable duplex with the amplification target circle. To aid in the transcription of the amplification target circle, the primer may be designed such that the 5' end has a 4–10 nucleotide sequence which is not complementary to the target amplification circle. This non-complementary region of the primer will aid in strand displacement during replication. Including a compatible helicase with the DNA polymerase will also facilitate strand displacement by uncoiling the nucleic acid being amplified.

Once the primer has annealed onto the amplification target circle, a DNA polymerase will attach at the site of the replication primer and extend. Given the similarities of the present assay to rolling circles replication, a DNA polymerase suitable for rolling circle replication would also likely be suitable for the present assay. The preferred nucleotides of the present invention lack any 5' to 3' exonuclease activity, and displace any nucleic acid that has annealed to the amplification target circle. This strand displacement action is required to synthesize the repeated copies of the amplification target circles which comprise the tandem-sequence DNA. Suitable DNA polymerases include *E. coli* DNA polymerase I, phage M2 DNA polymerase, T5 DNA polymerase, PRD1 DNA polymerase, and φ29 DNA polymerase.

Tandem-sequence DNA is generated by the DNA polymerase repeatedly copying the amplification target circle. The assay mixture may be optimized for the DNA polymerase selected. This reaction mixture should contain deoxynucleoside triphosphates as well as Mg++. The DNA polymerase selected should be a highly processive enzyme. The tandem-sequence DNA which is generated will be a concatamer consisting of repeated transcripts complementary to the amplification target circle, having repeating regions complementary to the stuffer region and the target hybridization end regions.

FIG. 5 illustrates the production of tandem-sequence DNA. Amplification target circle 24 is shown tethered to target nucleic acid 12. On the target amplification circle is a primer complementary sequence 27. When the cognate primer is added to a mixture containing the amplification target circle, the primer will hybridize to the amplification target circle. A DNA polymerase is then able to produce a single, repeating transcript of the amplification target circle. The amplification target circle is shown having two sequences 21, 23 complementary to a restriction site and one sequence of a detection probe site. The tandem-sequence DNA produced will be repeated sequences complementary to the amplification target circle. Thus the tandem-sequence DNA 50 will have, at regularly repeating intervals, restriction enzyme sites 41, 43 and detection probe complementary sites 45.

5. Cutting tandem-sequence DNA

Once the tandem-sequence DNA is generated, it may be digested into a number of uniform, non-tandem fragments using a nuclease. Each set of padlock probes will produce a range of fragment sizes. The presence of any fragment of a particular length will indicate that an amplification target circle was formed and repeatedly transcribed in a concatameric strand. This in turn will only occur if the targeted sequence was present such that ligation of the padlock probe was possible. Since the size of any one fragment is unique to the specific probe in the set of probes, the presence of the fragment is an indication of the presence of the targeted sequence.

Each padlock probe in a set is designed with the same restriction site so a single restriction enzyme may be used to digest the subsequent tandem-sequence DNA into non-tandem fragments. A large number of restriction enzymes that cut at various sites are commercially available from companies such as Amersham Pharmacia Biotech (Amersham Pharmacia Biotech Catalogue 1998).

The tandem-sequence DNA is digested by addition of a nuclease to the reaction mixture. The nuclease must be site specific. A region on the amplification target circle complementary to the nuclease restriction site produces a tandem-sequence DNA which has a nuclease restriction site at regular intervals. The nuclease restriction sites may be single strand cutting restriction enzymes. The use of these enzymes would allow digestion of the single stranded tandem-sequence DNA into detection fragments. Alternatively, a double strand restriction enzyme may be used. If this is used, at least part of the tandem repeat DNA must be double stranded.

In one embodiment, two restriction site complements would be present on each padlock probe in a set of padlock probes. Both sites would be present in the stuffer region proximate to the target hybridization end region. If both sites are identical, a single restriction enzyme may be used. Tandem-sequence DNA produced from ligated padlock probes with two restriction sites would be digested into two fragments. One fragment would consist of the sequence homologous to the target nucleic acid. The second fragment would be complementary to the stuffer segment of a probe. This second fragment would serve as the detection fragment in the embodiment.

FIG. 6 illustrates a digested set of fragments 55a–55g. Each fragment will be comprised of a constant region 51, which is the same for every fragment, and a variable length fragment which varies in length for each fragment. The variation is preferably in uniform increments such that the increase in fragment size is a standard number of bases. Although the fragments could be directly labeled by incorporation of detectable bases, it is preferred to use a detection probe to detect the fragments. The detection probe would hybridize onto detection probe complementary sequence 45. This sequence is on the constant region of the fragments, thus a single detection probe may be used to attach a detectable label to all of the fragments.

The tandem-sequence DNA is single stranded. When tandem-sequence DNA is digested by a restriction enzyme, the resulting fragments are also single stranded. The detection probe binds to one end of the detection fragment. In the presence of a DNA polymerase and dNTP bases, the detection probe may function as a second primer for the conversion of the single stranded detection fragments into double stranded detection fragments. The double-stranded detection fragments are subsequently detected.

6. Separation and detection of non-tandem fragments

Once the non-tandem fragments have been generated, the fragments must be separated and detected. A number of different systems are available for the separation and detection of DNA fragments of different sizes. For example, high performance liquid chromatography and mass spectrometry are two known methods to separate compounds of differing lengths by size. However, the preferred separation system is capillary array electrophoresis.

In addition, a number of miniaturized capillary electrophoresis separation devices are increasingly common as separation systems. These include "microprocessors", nanoprocessors, microchips, microplates and other devices. One such device is found in co-pending U.S. patent application Ser. No. 09/109,676 which describes a capillary electrophoresis chip in conjunction with a system for automatically loading the chip and conducting electrophoretic separation microchannels within the chip. Electrophoresis chips, like capillary electrophoresis, provide a separation length with an advantageous surface to volume ratio for joule heat dissipation.

Capillary array electrophoresis instruments allow automated electrokinetic sample loading from the wells of a microwell plate, and provide rapid analysis in a highly automated system. For example, the MegaBACE capillary array electrophoresis system (Molecular Dynamics, Sunyvale, Calif.) provides a system in which 96 capillaries are used in parallel. This system uses a pulse of electric current to inject a sample from each well into a capillary.

The capillaries in the array are filled with a separation media which may be adapted for the analysis of small DNA fragments. Free solution media, in which no sieving component is present, allows separation solely based on charge. For example, hydroxyethyl cellulose (HEC) may be used at a low concentration (less than 5%) as the separation media. Because the size of the DNA fragment will directly affect the charge of the molecule, the smaller molecules will migrate more rapidly, resulting in separation of the injected fragments by size. This media may be reused in several electrophoretic separations, after which the capillaries are filled with fresh separation media. Alternatively, the separation may use various sieving separation media, such as linear polyacrylamide. Once the samples are injected into the capillaries, an electric field in the capillaries effects sample migration toward a detection zone in each capillary. The detection zone of the capillary is scanned with a laser to stimulate fluorescence from fluorescent labels associated with the fragments. Optical detectors record the emitted fluorescence. The migration rate of the fragment from the injection to detection will be dependent on the size of the fragment.

Presently, one injection of a sample is possible every 2 hours on the MegaBACE system. Modification to the system would allow more frequent injections of the sample into capillaries. Pending U.S. patent application Ser. No. 09/352,281, hereby expressly incorporated by reference herein, further describes the capillary array electrophoresis system and discloses a method and apparatus for modification of a separation system to allow multiple injections into each capillary. In this procedure, samples could be injected every 20 minutes, followed by continuous detection after a number of samples are introduced into each capillary.

The detection fragments may be directly stained or labeled with radioactive labels, antibodies, luminescent dyes, fluorescent dyes, or enzyme reagents. Fluorescent dye is preferred. All of the detection fragments produced by one set of padlock probes should all be labeled with the same detectable label. The detection fragment may be labeled by the fluorescent dye by using a direct DNA stain, by incorporation of a labeled nucleotide into the DNA during synthesis of the tandem-sequence DNA, or by using a labeled detection probe. Preferably the fluorescent dye label has an excitation and emission wavelength such that the dye may be excited at one wavelength and detected at a second wavelength. In addition, the dye should be detectable in the presence of other dyes.

Direct DNA stains include acridine orange, ethidium bromide, ethidium monoazide, Hoechst dyes, fluorescein and rhodamine. These are available from commercial sources such as Molecular Probes, Eugene, Oreg.

An alternative to direct staining of the DNA fragments is incorporation of labeled dNTP bases into the synthesized tandem-sequence DNA. The detection fragments produced from the tandem-sequence DNA have the labeled bases incorporated into the detection fragment. Detection labels which may be associated with nucleotide bases include fluorescein, a cyanine dye or BrdUrd.

A final alternative is the use of a detection probe. A detection probe is a labeled oligonucleotide sequence having a sequence which is able to form specific and stable hybridization with the detection probe complementary sequence found in the constant stuffer region of certain sets of padlock probes. The above listed direct stain and synthesis labeling may be used to label the detection probe. As noted above, the detection probe may be used to create a region of double-stranded DNA enabling a restriction enzyme that cuts double stranded DNA to be used to create non-tandem detection fragments.

The method is further illustrated in the examples below.

EXAMPLE 1

25 Loci Single Nucleotide Polymorphism Analysis.

Analysis of single nucleotide polymorphisms allows determination of variants that differ at one base at a specific genomic locus. Several features of single nucleotide polymorphisms make the variation useful as a source of genomic information. First, some single nucleotide polymorphisms are located in expressed genes and may correlate with phenotypic expression. Second, single nucleotide polymorphisms are relatively common, occurring at about one in 200–2000 bases. These polymorphisms are found throughout the genome. There are millions of single nucleotide variants in the human genome which are distributed throughout the genome, making these variants useful markers. Finally, single nucleotide polymorphisms are commonly bi-allelic (i.e. having two base alternatives at the polymorphic site). This simplifies allele calls allowing for a binary allele scoring system.

To analyze 25 single nucleotide polymorphisms, two sets of 25 allele-specific padlock probes are used in each assay container. The variable section of each probe's stuffer regions varies in length by two bases. The padlock probes range in size from 50 to 100 bases when ligated into an amplification target circle. The target hybridization end regions are each designed to anneal to a single genome locus. The padlock probe anneals onto the target genomic DNA such that the ends are separated by a gap. Located at each gap is the targeted polymorphism. By using two sets of padlock probes, each allele may be separately investigated. The first set of padlock probes would be directed to detect one allelic variant and the second set of padlock probes would be directed to detect the second variant. By designing the padlock probes with the variant in a gap section between the target hybridization end regions, a single padlock probe set could be used to detect both variants.

In each reaction container, denatured genomic DNA is combined with the set of 25 padlock probes and gap oligonucleotides and allowed to hybridize. The 25 probes hybridize at 25 loci on the target genomic DNA. Ligase is added and under ligation conditions, the probe will seal to form an amplification target circle if the single nucleotide variant of interest is present. If so, the gap oligonucleotide will completely anneal, allowing ligation. However if the variant is not present, the gap oligonucleotide will have a terminal base mismatch, preventing ligation.

Following the ligation reaction, a replication primer, a strand displacement DNA polymerase, and dNTPs are added to each container. The primer is complementary to a sequence present in all of the padlock probes. After the primer has been sealed by ligation, the DNA polymerase will produce tandem-sequence DNA by rolling circle amplification.

Each padlock probe contains an identical restriction enzyme site complement. The tandem-sequence DNA generated from the probes may be digested with the restriction enzyme to produce detection fragments. These detection fragments will range from 50–100 bases, and will correspond to the original size of the amplification target circles. Fragments will be present only for those alleles which were successfully amplified by rolling circle amplification, indicating that these alleles were present in the genomic DNA assayed. Each probe has a detection probe region that is identical for all of the probes in a set. A detection probe is added to each assay container and binds to each detection fragment.

Each container is separately analyzed by capillary electrophoresis. Using a sizing ladder, the data from each capillary assay may be compared and scoring of each variant is simplified. If a fragment of a specified size is present in one reaction and not the other, the targeted genomic DNA is homozygous for the corresponding allele. If fragments of one size are present in both reactions, the targeted DNA is heterozygous.

EXAMPLE 2

In a second example, throughput is further increased by the use of different labels to detect the presence of multiple fragments of the same length. In this method, three sets of padlock probes are provided. Each set contains 30 probes. Each individual probe in each set is designed to assay a variant at a nucleic acid locus. If the variant of interest is present, each probe in a set will, under ligation conditions, ligate to form an amplification target circle. Tandem-sequence DNA may be generated from the amplification target circle. The tandem-sequence DNA generated is then cut at a restriction enzyme site. The resulting detection fragments produced from each probe in the set of probes differ in length by two bases. If the length of the detection fragments varies from 40 to 100 bases long, 30 variants may be assayed with each set of probes. The probes in all three sets of probes have common restriction site complementary sites and primer complementary sites. The ligation, amplification and restriction steps may be performed in a single reaction container, such as a microplate well. For each set of probes, a maximum of 30 sets of detection fragments would be generated. Each set of padlock probes would have a detection probe sequence that is the same for each probe in the set but different from the detection probe sequence of each of the other two sets of padlock probes. Thus three detection probes would be needed to detect the detection fragments. Each of the three detection probes would have a unique optically detectable label. Analysis of the detection fragments on an analytical system which is able to discriminate four colors would allow detection of three fragments of the same size at the same time, with each fragment identified by color. The fourth color detectable by the analytical system would be used in a standardized size DNA ladder to aid in discrimination of variants. This gives the analytical system a standardized reference point for simplified detection. In this manner, the three sets of probes could produce detection fragments of the same sizes which would be distinguishable. In a capillary array electrophoresis system, the three sets of probes could be analyzed in a single capillary in a capillary array electrophoresis system. This would allow higher throughput.

The multiplexing methods described allow much greater throughput for each assay. For example, in one method each set of padlock probes contains 30 probes which assay 30 variants and may produce 30 DNA fragments, each differing in length by 2 nucleotides. By labeling the fragments with different detectable labels, fragments of the same size may be differentiated by the detector. Thus three sets of padlock probes may be used in the reaction with a four-color detector while reserving one color for a standard DNA-sizing ladder. Thus, in a single reaction volume, 90 separate variants may be analyzed using many of the same reagents. For these 90 variants, the padlock probes will be designed such that a single primer may be used for the amplification of all of the probes.

If 90 variants may be analyzed in a single well, in a 96-well plate 8640 variants may be analyzed. If the padlock probes are designed to detect the presence of genes, 8640 genes may be identified. If the padlock probes are used to make allele calls for single nucleotide polymorpnisms, the analysis method allows 4320 allele calls in a biallelic system. As described, a 96-well capillary array electrophoresis system is able to inject 96 samples at a time and analyze the samples in parallel. Presently, one plate may be processed every two hours in each system. At this rate, 103,680 variants may be analyzed each day on each 96 capillary array electrophoresis system. Modification of the system to allow more frequent loading of samples would further increase system throughput. Because the fragments analyzed are relatively small, the fragments will migrate through the capillary relatively quickly. An injector could repeatedly inject samples into the system such that several plates of samples are loaded onto a capillary. The samples would be repeatedly injected into the capillary such that the samples are detectably separated when the samples reach the detector. This method, described in U.S. patent application Ser. No. 09/352,281, hereby expressly incorporated by reference herein, would allow for a ten-fold increase in sample throughput to a rate of 1,036,000 variants detected per day for each 96 capillary electrophoresis system.

We claim:

1. A plurality of padlock probes, each probe comprising:
a nucleic acid sequence, the sequence including two target hybridization end regions on opposing ends of each padlock probe, the target hybridization end regions complementary to a target hybridization region on a single strand target nucleic acid sequence, wherein the target hybridization end regions may hybridize to the single strand target nucleic acid sequence to form a probe/target duplex, wherein each pair of target hybridization end regions are proximate to each other when hybridized to the target nucleic acid strand; and
a stuffer region located between said target hybridization end regions, said stuffer region having a primer complementary sequence and a restriction site complementary sequence, wherein each of said padlock probes has the same primer complementary sequence and restriction site complementary sequence;
wherein each probe may act as a template for production of tandem sequence DNA by ligation and amplification of the probe if a specific target nucleic sequence is present;
wherein tandem sequence DNA produced from each template padlock probe may be segmented into a set of non-tandem detection fragments of a discrete length, wherein the discrete length of detection fragments produced from each padlock probe differs in length from any detection fragment produced from any other padlock probe in the plurality of padlock probes.

2. The plurality of padlock probes of claim 1, wherein the target hybridization end regions of each padlock probe are complementary to a target hybridization region on the single strand nucleic acid such that there is a gap between said two target hybridization end regions.

3. The plurality of padlock probes of claim 2, wherein each gap is at least 4 bases in length.

4. The plurality of padlock probes of claim 2, wherein the locus on the target nucleic acid opposite the gap is a locus of a single nucleotide polymorphism.

5. The plurality of padlock probes of claim 1, wherein each target hybridization end region is at least 10 bases long.

6. The plurality of padlock probes of claim 1 wherein each stuffer region includes a constant region and a variable region, wherein the constant region is identical for each of the padlock probes of the plurality of padlock probes and wherein the variable region is non-identical for each of the probes in the plurality of padlock probes, wherein the constant region contains the primer complementary sequence, and wherein the variable region is of a different length for each of padlock probes in the plurality of padlock probes.

7. The plurality of padlock probes of claim 6 further comprising two restriction site complementary sequences in said constant region of the stuffer region, each restriction site complementary sequence located proximate to one of the two target hybridization end regions and each of said two restriction site complementary sequences identical for each of the plurality of padlock probes.

8. The plurality of padlock probes of claim 7, wherein the two restriction enzyme site complementary sequences are the same.

9. The plurality of padlock probes of claim 1 wherein the discrete length of detection fragments produced from each padlock probe differs in length from any other detection fragment produced from any other padlock probe in the plurality of padlock probes by at least two bases.

10. The plurality of padlock probes of claim 6 wherein the restriction enzyme site template is a single strand restriction enzyme site template.

11. The plurality of padlock probes of claim 6 wherein the restriction site template is for a restriction enzyme that cuts double-stranded DNA and wherein the restriction site template is located within the primer complementary sequence.

12. A method for high throughput analysis of genetic loci, the method comprising the steps:
   a) providing a target nucleic acid sample;
   b) combining the target nucleic acid sample with a plurality of padlock probes to form padlock probe/target hybrids, wherein each probe is a nucleic acid sequence including,
      two target hybridization end regions on opposing ends of the padlock probe, the target hybridization end regions complementary to a target hybridization region on a single strand target nucleic acid sequence, wherein the target hybridization end regions hybridize to the single strand target nucleic acid sequence to form a probe/target duplex, wherein each pair of target hybridization end regions are proximate to each other when hybridized to the target nucleic acid strand, and
      a stuffer region located between said target hybridization end regions, said stuffer region having a primer complementary sequence and restriction site complementary sequence, wherein each of said plurality of said padlock probes has the same primer complementary sequence and restriction site complementary sequence;
   c) mixing ligase with the padlock probe/target nucleic acid duplex to form a ligation mixture, and incubating the ligation mixture under conditions that promote ligation of the padlock probes to form amplification target circles;
   d) mixing a primer which is complementary to said primer complementary sequence with the amplification target circles, and incubating the primer/amplification target circles mixture under conditions that promote hybridization between the amplification target circles and the primers;
   e) mixing a DNA polymerase with the primer/amplification target circles mixture, to produce a rolling circle replication mixture, and incubating the rolling circle amplification mixture under conditions that promote rolling circle replication of the amplification target circles,
      wherein replication of the amplification target circles results in the formation of tandem sequence DNA;
   f) cutting each tandem sequence DNA at the generated restriction enzyme site into sets of non-tandem DNA fragments of a discrete length, wherein each amplification target circle produces tandem sequence DNA that is cut into sets of non-tandem DNA fragments of a unique discrete size;
   g) separating by length said sets of non-tandem DNA fragments; and
   h) detecting said sets of separated non-tandem DNA fragments.

13. The method of claim 12, wherein steps b, c, d, e and f all are carried out in a single reaction container.

14. The method of claim 12 wherein the step of combining the target nucleic acid sample with a plurality of padlock probes includes combining the target nucleic acid with 30 padlock probes.

15. The method of claim 13 wherein each padlock probe will be ligated to form an amplification target circle only if a specific polymorphism at a genomic loci is present on the target nucleic acid sequence.

16. The method of claim 13 wherein each padlock probe will be ligated to form an amplification target circle only if a specific sequence at a specific locus on the target nucleic acid is present.

17. The method of claim 13 wherein each padlock probe will be ligated to form an amplification target circle only in the presence of a target mRNA molecule.

18. The method of claim 13 wherein each padlock probe will be ligated to form an amplification target circle only in the presence of a target cDNA molecule.

19. The method of claim 12 wherein the padlock probe includes a labeled secondary probe complement region on each of the plurality of padlock probes whereby step h may be effected by adding a labeled secondary probe that hybridizes to the secondary probe complement region and detecting the label on the secondary probe whereby each set of fragments may be detected by detecting the same secondary probe label.

20. The method of claim 19, wherein the label is a fluorescent dye.

21. The method of claim 12 wherein step g is effected by capillary electrophoretic separation.

22. The method of claim 21 further including prior to step g the step of adding a sizing ladder to the sets of non-tandem DNA fragments.

23. The method of claim 12, wherein each of the non-tandem DNA fragments of each set of non-tandem DNA fragments differs in length from any other non-tandem DNA fragment of any other set of non-tandem DNA fragments by at least 2 bases.

24. The method of claim 23 wherein non-tandem DNA fragments produced are between 20 to 150 bases in length.

25. The method of claim 12 wherein the step of cutting the tandem sequence DNA at the generated restriction site includes cutting the tandem sequence DNA at a single stranded restriction enzyme cutting site.

26. The method of claim 20 wherein the step of cutting each tandem sequence into sets of non-tandem fragments is effected by providing a plurality of padlock probes wherein each padlock probe has a first and a second restriction enzyme template each located proximate to one of the two target hybridization end regions such that tandem sequence DNA produced by each of the plurality of padlock probes may be cut into two sets of fragments, a first set of fragments complementary to the two target hybridization end regions and a second set of fragments wherein the second set of fragments generated from any tandem sequence DNA is of different length for each tandem sequence DNA generated from each unique amplification target circle.

27. The method of claim 26 wherein the first and second restriction enzyme site templates are the same restriction enzyme template.

28. The method of claim 12 wherein the method detects variation in single nucleotide polymorphisms.

* * * * *